United States Patent [19]

Zhang et al.

[11] Patent Number: 5,786,219
[45] Date of Patent: Jul. 28, 1998

[54] MICROSPHERES WITH FLUORESCENT SPHERICAL ZONES

[75] Inventors: Yu-Zhong Zhang; Courtenay R. Kemper; Richard P. Haugland, all of Eugene, Oreg.

[73] Assignee: Molecular Probes, Inc., Eugene, Oreg.

[21] Appl. No.: 740,184

[22] Filed: Oct. 28, 1996

[51] Int. Cl.$^6$ .................... G01N 33/546; G01N 33/533
[52] U.S. Cl. .................... 436/523; 436/533; 436/534; 436/531; 422/82.07; 422/82.08; 428/402; 428/402.24; 428/403; 428/407; 523/201; 523/200
[58] Field of Search .................... 436/523, 533, 436/534, 531; 422/82.07, 82.08; 428/402, 402.24, 403, 407; 523/201, 200

[56] References Cited

U.S. PATENT DOCUMENTS

| | | | |
|---|---|---|---|
| 4,326,008 | 4/1982 | Rembaum | 428/403 |
| 4,609,689 | 9/1986 | Schwartz et al. | 523/202 |
| 4,767,205 | 8/1988 | Schwartz et al. | 356/71 |
| 4,774,339 | 9/1988 | Haugland et al. | 548/405 |
| 4,916,711 | 4/1990 | Boyer et al. | 372/53 |
| 5,136,005 | 8/1992 | Hermes | 526/292.3 |
| 5,187,288 | 2/1993 | Kang et al. | 548/110 |
| 5,189,029 | 2/1993 | Boyer et al. | 514/64 |
| 5,248,782 | 9/1993 | Haugland et al. | 548/110 |
| 5,274,113 | 12/1993 | Kang et al. | 548/405 |
| 5,286,803 | 2/1994 | Lindsay et al. | 525/329.7 |
| 5,326,692 | 7/1994 | Brinkley et al. | 435/6 |
| 5,338,854 | 8/1994 | Kang et al. | 548/110 |
| 5,433,896 | 7/1995 | Kang et al. | 252/700 |
| 5,446,157 | 8/1995 | Morgan et al. | 546/13 |
| 5,573,909 | 11/1996 | Singer et al. | 435/6 |

OTHER PUBLICATIONS

Bangs, Uniform Latex Particles, 1984, Seragen, Inc. Indianapolis, IN, pp. 1–65.
Jones, et al. Proc. Int. Conf. Lasers, 18, 375–382 (1996).
Jones, et al. Proc. SPIE 2968, 65–74 (1996).
Pekcan et al. Physical Review Letters 61, 641–644 (1988).

*Primary Examiner*—Toni R. Scheiner
*Attorney, Agent, or Firm*—Allegra J. Helfenstein; Anton E. Skaugset

[57] ABSTRACT

The invention describes novel fluorescently labeled microspheres, where the microspheres possess at least one internal fluorescent spherical zone. The invention also describes the method of preparing the novel microspheres, the method of calibrating microscopy instrumentation using the novel microspheres, the method of using the novel microspheres as distinct labels for combinatorial analysis and the use of the labeled microspheres as tagging agents and tracers.

28 Claims, 4 Drawing Sheets

Figure 1

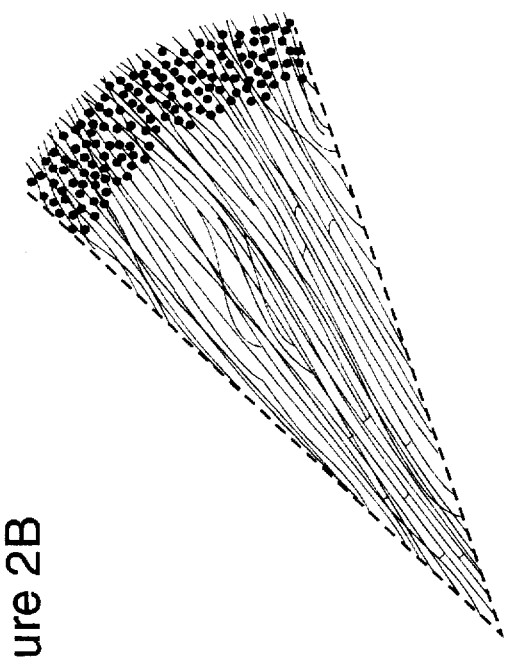
Figure 2A
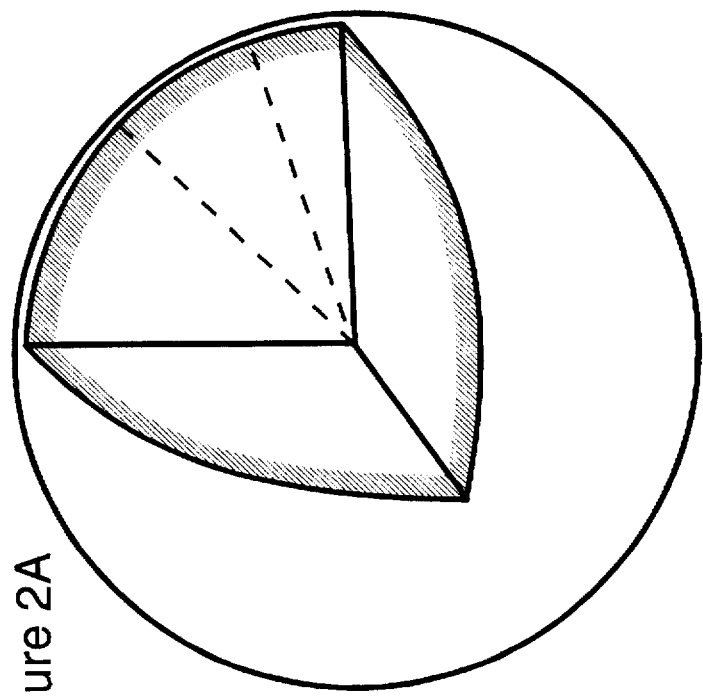
Figure 2B
Figure 2

Figure 3
Figure 3A
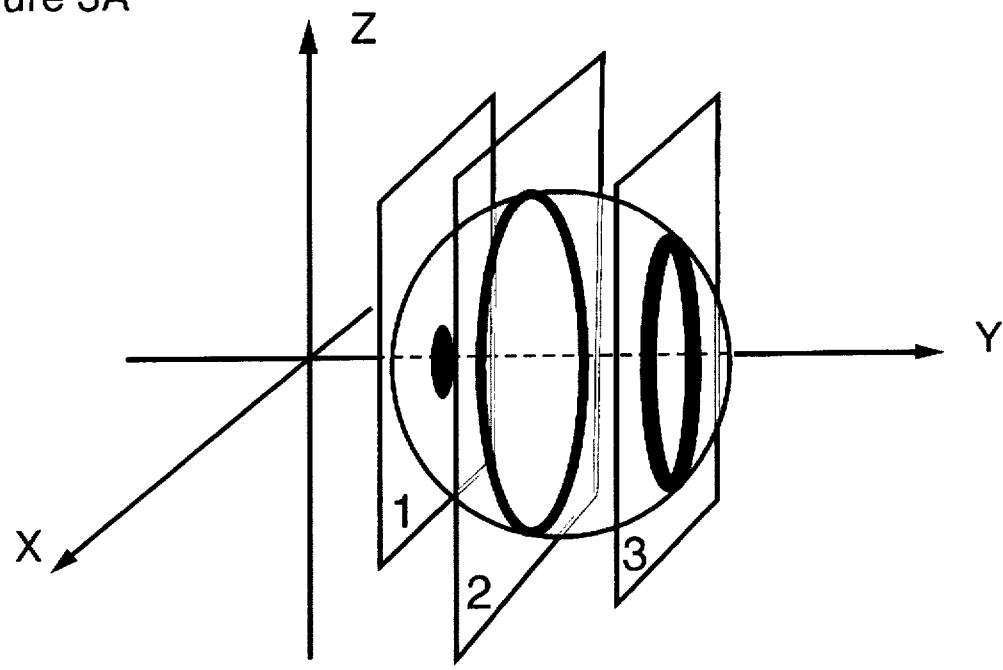
Figure 3B
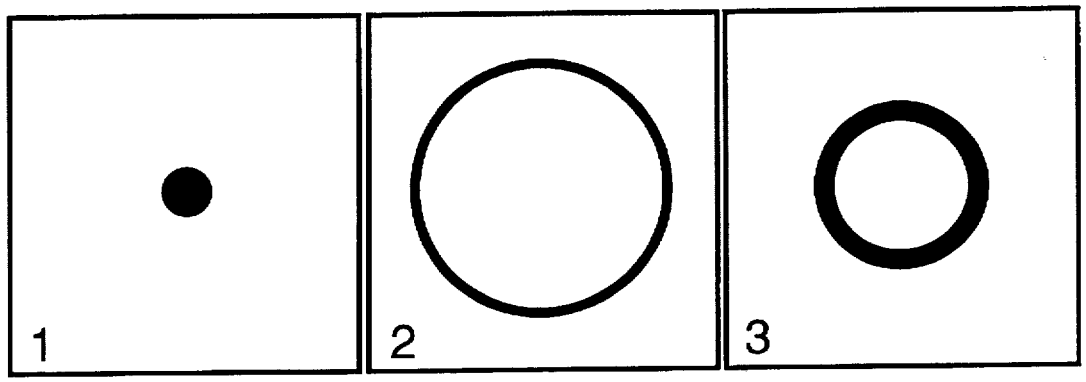

Figure 4
Figure 4A
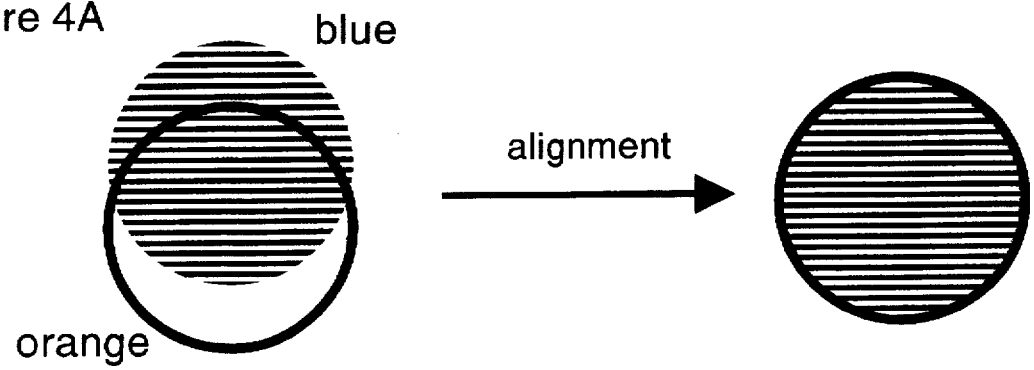
Figure 4B
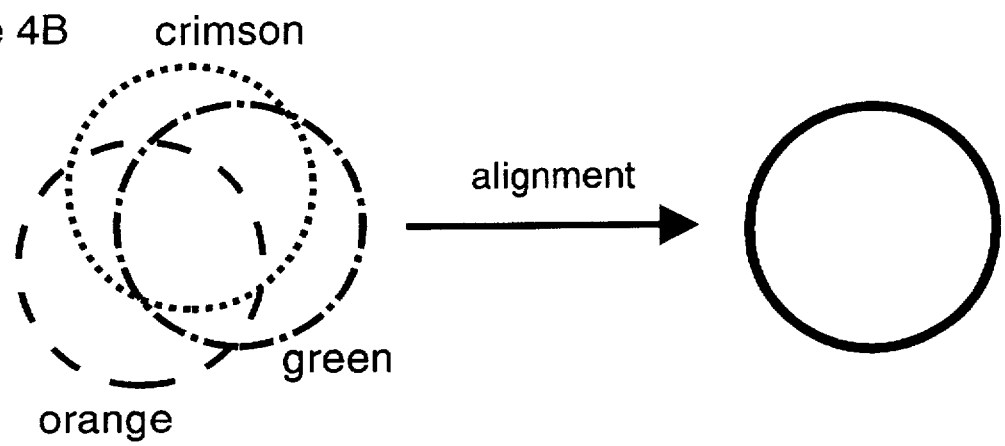
Figure 4C
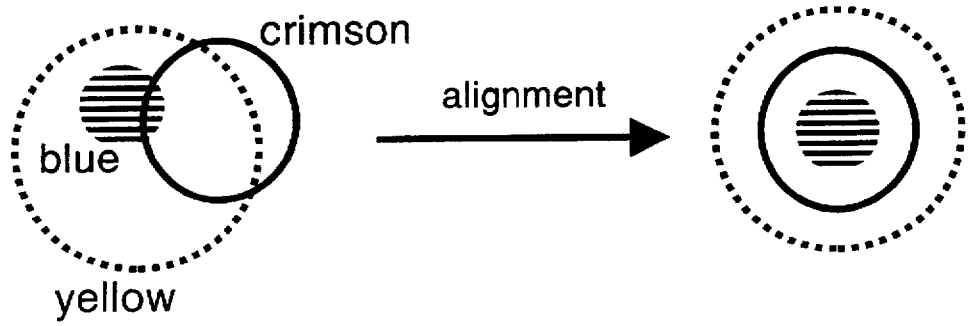

MICROSPHERES WITH FLUORESCENT SPHERICAL ZONES

This invention was made with Government support under Grant No. #1R43A132831-01 awarded by the National Institutes of Health. The Government has certain rights in this invention.

FIELD OF THE INVENTION

The invention describes polymer microspheres possessing at least one internal spherical zone labeled with one or more fluorescent dyes. The resulting microspheres are useful as standards for instrument calibration, particularly confocal microscope calibration, and as tracers.

BACKGROUND TO THE INVENTION

Polymeric microspheres labeled with fluorescent dyes (fluorescent microspheres) are most commonly used in applications that can benefit from the use of monodisperse, chemically inert, biocompatible particles that radiate detectable fluorescence and that can be coupled to members of specific binding pairs so as to make them bind to a particular substance in a sample. However, fluorescent microspheres have also found use in a wide variety of other applications, including instrument calibration and tracing. There are predominantly two types of labeled microspheres: surface labeled or labeled throughout. For surface-labeled microspheres, a monolayer of dye is typically deposited on the microsphere surface using a fluorescent protein coating or by covalent attachment of the desired label. Fluorescent microspheres labeled essentially throughout their entire volume are prepared either by copolymerization of a fluorescent monomer (the dye is covalently bound to a monomer prior to polymerization) or by batch staining of preformed microspheres with a dye that is soluble in the polymer microsphere.

Recent advances in microscope instrumentation, such as confocal laser scanning microscopy and wide-field microscopy coupled with data deconvolution, allow the user to analyze a sample in three dimensions, to record a single optical section of the specimen having a preferred thickness, and to acquire and analyze information at multiple fluorescence emission wavelengths (simultaneously or sequentially), often using multiple excitation wavelengths. Computer restoration permits the reconstruction of essentially three-dimensional images of the sample. The complexity of this instrumentation is such that many of the optical parameters of the microscope are not readily calibrated using the methods and standards of conventional microscopy. In particular, it is difficult to calibrate dimensions along the z-axis of the sample (perpendicular to the plane of the microscope slide), which can be measured as the set of distances between the surface of the microscope slide and the coverslip. Users of such microscopes therefore employ a variety of standards to evaluate their instrument performance, such as etched test patterns, integrated circuits, diatom frustules immersed in a fluorescent solution, or biological cells stained with single or multiple dyes.

Each type of commonly used calibration standard possesses some limitations. The two-dimensional nature of etched patterns and integrated circuits offers poor calibration along the z-axis. Diatoms, as natural organisms, possess irregularity in size and structure. Biological cells are also irregular in shape and can exhibit very different fluorescence emissions at different parts of the same cell. In contrast, the unique microspheres of this invention, which when viewed in a cross-section that includes the center of the microsphere (hereafter referred to as an equatorial cross-section), display one or more distinct concentric rings of fluorescence, provide uniform standards of known geometry, fluorescence intensity and staining pattern that facilitate instrument alignment and computer-generated image reconstruction. In addition, the dyes inside the microsphere are protected from solvent effects, such as pH variation, making them both brighter and less prone to photobleaching than surface-stained microspheres. Furthermore the ability to select fluorescent excitation and emission spectra from ultraviolet to infrared wavelengths permits the correction of chromatic aberration and other optical artifacts. Also, the ability of microscopes to reconstruct the staining pattern of single microsphere makes it possible to distinguish and identify a single microsphere within a mixture of microspheres that have a wide variety of patterns, colors, fluorescence intensities and sizes.

BRIEF DESCRIPTION OF THE DRAWINGS

FIG. 1.

FIG. 1A depicts a microsphere having a single distinct fluorescent ring near the microsphere's outer surface.

FIG. 1B depicts a microsphere having a single distinct fluorescent ring located well within the interior of the microsphere.

FIG. 1C depicts a microsphere having a distinct fluorescent ring near the microsphere's outer surface in conjunction with an additional distinct fluorescent ring located well within the interior of the microsphere.

FIG. 1D depicts a microsphere having multiple distinct fluorescent rings within the interior of the microsphere, such that they are partially coincident.

FIG. 1E depicts a microsphere having a distinct fluorescent ring near the microsphere's outer surface in conjunction with a concentric fluorescent disk located at the core of the microsphere.

FIG. 1F depicts a microsphere having multiple distinct fluorescent rings in conjunction with a fluorescent disk at the core of the microsphere.

FIG. 2: FIG. 2A shows a cut-away view of a microsphere that has been shallowly stained with a fluorescent label, as indicated by cross-hatching. The dashed lines of FIG. 2A indicate the expanded view shown in FIG. 2B, wherein dye molecules (indicated by dark dots) are depicted as incorporated into the polymeric matrix of the microsphere (indicated by partially cross-linked lines).

FIG. 3: FIG. 3A shows a microsphere of the present invention that has been shallowly stained with a fluorescent label. Planes 1, 2 and 3 represent cross-sections of the microsphere in the X–Z plane and correspond to two-dimensional views 1, 2 and 3 shown in FIG. 3B.

FIG. 4: FIG. 4 shows the use of three specific embodiments of the invention to correct the alignment of an instrument, wherein each of FIGS. 4A, 4B and 4C shows a cross-section of the microsphere before and after alignment. In each case, proper alignment of the instrument is readily evidenced by the restoration of the accurate representation the microsphere.

FIG. 4A shows the use of a uniform fluorescent blue-stained microsphere that is additionally shallowly stained with a fluorescent orange label.

FIG. 4B shows the use of a microsphere that has been shallowly stained with three fluorescent labels, yielding coincident spherical zones that possess crimson, orange and green fluorescence, respectively.

FIG. 4C shows the use of a microsphere that is labeled with a fluorescent blue internal disk, a distinct fluorescent crimson ring located well within the interior of the microsphere, and a fluorescent yellow shallow stain.

Figure 1A:
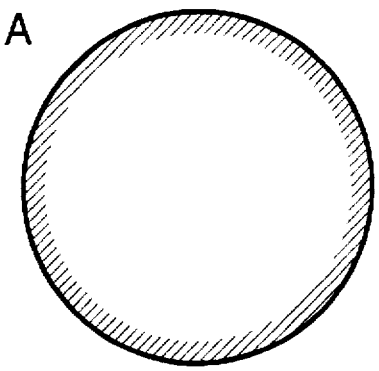
FIGS. 1A–1F depict several distinctive staining patterns suitable for the microspheres of the present invention. Each microsphere is shown in equatorial cross-section.
Figure 1B:
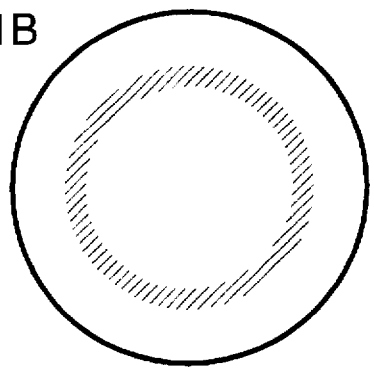

SUMMARY OF THE INVENTION AND DESCRIPTION OF PREFERRED EMBODIMENTS OF THE INVENTION

The invention describes novel fluorescent microspheres that are labeled so as to possess at least one fluorescent spherical zone, such that following excitation of the particle at an appropriate wavelength, an equatorial cross-section exhibits at least one ring of fluorescence emission. Individual microspheres may exhibit multiple rings, or may optionally exhibit a fluorescent disk, that may or may not overlap with each other when viewed in cross-section. Fluorescent spherical zones can also differ in excitation and emission properties and fluorescence intensity. The polymeric microspheres can differ in diameter and polymer composition. The size, number and color characteristics of the rings and disks is controlled by varying parameters in the staining protocol or by changing the methods used to prepare the microspheres.

The invention further describes methods for preparing and using the spherically labeled microspheres. Methods of using the patterned microspheres for calibrating microscopes and as labels and tagging agents are described. Also described are kits that include multiple fluorescent microspheres that can be distinguished from each other using optical imaging of the staining patterns in three-dimensions.

The microspheres of this invention possess one or more distinct, fluorescently labeled, spherical zones. By "spherical zone" is meant a fluorescent zone that is present within the polymer microsphere and concentric with the microsphere, such that any equatorial cross-section of the microsphere evidences a distinct fluorescent ring, the diameter of which ring is less than the diameter of the microsphere. Optionally, the microspheres of the present invention are stained with additional fluorescent spherical zones, or with an internal solid spherical zone such that an equatorial cross-section evidences a distinct fluorescent disk. The staining patterns of the microspheres of the invention are necessarily isotropic, so that any equatorial cross-section is equivalent to any other equatorial cross-section. Therefore, for ease of illustration, the spherical zones are described as either rings or disks. It is understood, however, that these terms encompass the three-dimensional configuration that corresponds to a ring (i.e. a spherical shell) or a disk (i.e. a solid sphere).

The microspheres of this invention are spherical in shape, and have a diameter of between about 2–100 μm, and are preferably less than 50 μm in diameter. More preferably, the microspheres have a diameter of about 4–16 μm, most preferably about 8–16 μm. Typically, the labeled microspheres of the invention are of a size sufficient to obtain at least 10 optical cross-sections along the z-axis. For example, performing this type of cross-sectional analysis on a microsphere having a diameter of 2 μm would generate ten optical sections each having an average thickness of 0.2 μm, well within the resolution of contemporary confocal laser scanning microscopes.

For all embodiments of the invention, the microspheres possess at least one distinct fluorescent-labeled spherical zone, such that when the microsphere is viewed in an equatorial cross-section, the cross-section displays a staining pattern that includes at least one distinct fluorescent ring. The distinct fluorescent ring is essentially circular and concentric with the microsphere itself.

'Distinct', as used herein, means readily distinguishable. That is, the fluorescent ring is readily distinguishable either by spectral characteristics or by fluorescence intensity from the remainder of the cross-section, as well as from additional fluorescent rings or disks that are optionally present in the cross-section. The boundaries, or edges, of the ring are distinguishable and are not diffuse, so that the width of the ring is readily determinable.

Where a fluorescent ring is readily distinguishable by spectral characteristics, typically the fluorescence emission maximum of each distinguishable ring is separated by at least 5 nm, preferably by at least 10 nm and more preferably by at least 20 nm. In a preferred embodiment, by utilizing independent optical filters and optical channels of an instrument (such as a confocal laser scanning microscope) each distinct fluorescent spherical zone is capable of being separately excited, and separately detected, and the fluorescence emissions of each spherical zone can be visibly distinguished. However, the ability of advanced imaging equipment to discriminate between closely separated emissions and to accurately quantitate fluorescence intensities makes it possible to utilize such instruments to reliably differentiate between individual microspheres, even when the distinct staining patterns of the respective microspheres may not be distinguishable by the human eye.

In one embodiment, the fluorescent ring is distinct because the maximum fluorescence intensity of the ring is at least 20% greater than the average background fluorescence of the microsphere, when measured at the wavelength of maximum fluorescence of the ring, and when the average background fluorescence of the microsphere excludes the contribution of the fluorescence of the ring. An average background fluorescence intensity calculated in this manner is herein referred to as an "adjusted average fluorescence intensity". In another embodiment, a distinct fluorescent ring is a ring wherein the concentration of the fluorescent dye or dyes present within the fluorescent spherical zone is at least 10-fold greater than the concentration of the same dye or dyes in any region outside the fluorescent spherical zone.

The "width" of a fluorescent ring, as described herein, means the shortest measured distance between the outside radius and the inside radius of the fluorescent ring. For all embodiments, the width of each fluorescent ring is at least 0.2 μm, and is no greater than the equivalent of 35% of the radius of the labeled microsphere. That is, a fluorescent ring within a 4 μm microsphere is between 0.2 μm and 0.7 μm wide; a fluorescent ring in a 15 μm microsphere is between 0.20 μm and 2.63 μm wide. Preferably, the fluorescent rings have a width of at least 0.5 μm and the width of each fluorescent ring is no greater than 30% of the radius of the microsphere, more preferably no greater than 25% and yet more preferably no greater than 20% of the radius of the microsphere. Typically, the width of the fluorescent rings is less than 3 μm, more typically less than 2 μm.

The fluorescent ring may be at or near the polymer microsphere's interior surface (as shown in FIG. 1 A) although the ring must be within the microsphere itself, rather than on the exterior surface, in order for the microsphere to possess the advantages arising from internal incorporation of the dye. In this embodiment, the ring has an outer diameter that is essentially equal to the diameter of the microsphere itself. This type of microsphere is also referred to herein as 'shallowly stained'. In another embodiment, the ring has an outer radius that is essentially equal to the radius of the microsphere itself and an inside radius greater than 75% of the radius of the microsphere itself, more typically, an inside radius greater than 80% of the radius of the microsphere. In yet another embodiment, the ring is present well within the interior of the microsphere, in the zone between the center of the cross-section and the surface (for example, as shown in FIG. 1B).

In the simplest embodiment of the invention, the microsphere of the invention is labeled with a single distinct fluorescent spherical zone, yielding a single distinct fluorescent ring. Preferably the microspheres of this embodiments possess a fluorescent ring having an outer diameter essentially equal to the diameter of the microsphere itself.

Figure 1C:
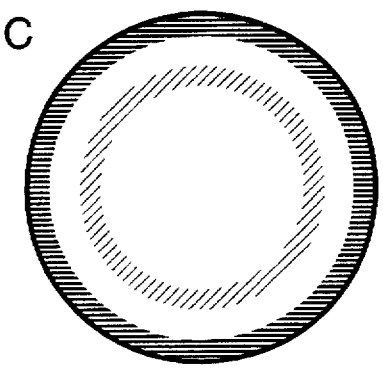
Figure 1D:
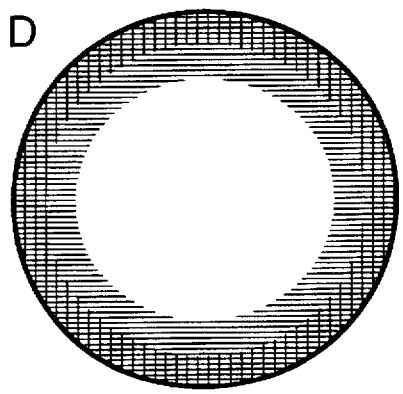

In another embodiment of the invention, the microsphere possesses one or more additional fluorescent spherical zones, such that an equatorial cross-section possesses two or more distinct fluorescent rings. The rings are readily distinguishable from each other and from the remainder of the cross-section, and may be non-coincident, i.e. discrete rings (as shown in FIG. 1C) having the same or different spectral properties, or may be fully or partially coincident and have detectably distinct spectral properties (an example of partially coincident multiple rings is shown in FIG. 1D).

In yet another embodiment of the invention, an equatorial cross-section of the microsphere possesses one or more distinct fluorescent disks in addition to at least one distinct fluorescent ring. The fluorescent disk is readily distinguishable either by spectral characteristics or by fluorescence intensity from the remainder of the cross-section, as well as from additional fluorescent rings or disks that are optionally present in the cross-section. The fluorescent disk may be non-coincident with any fluorescent rings having the same or different spectral properties, or may be fully or partially coincident with any fluorescent rings or additional disks and have detectably distinct spectral properties.

Figure 1E:
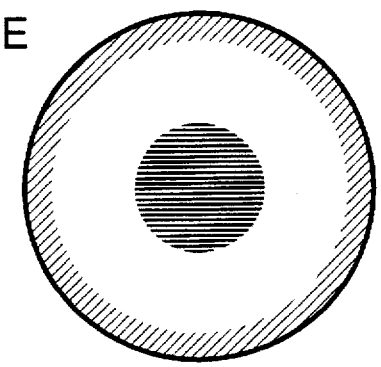
Figure 1F:
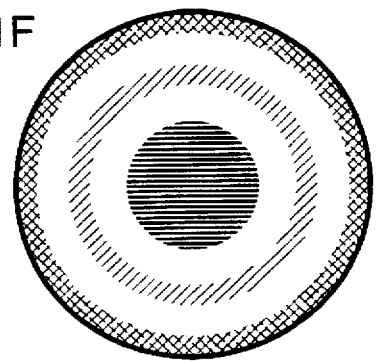

Each fluorescent disk is concentric with the microsphere itself, and each disk has a diameter of at least 0.4 μm and as large as the diameter of the microsphere itself. Where the diameter of the fluorescent disk is essentially equal to the diameter of the microsphere, the resulting microsphere possesses essentially uniform fluorescent staining throughout the interior of the microsphere. In one embodiment of the invention, the fluorescent disk has a diameter no greater than 70% of the diameter of the microsphere itself. In another embodiment of the invention, a microsphere possesses a single distinct fluorescent disk in addition to a single distinct fluorescent ring (as shown in FIG. 1E). In another embodiment of the invention, a microsphere possesses a single fluorescent disk in conjunction with multiple distinct fluorescent rings (as shown in FIG. 1F). Where the disk produces essentially uniform staining, the microsphere must also possess one or more distinct fluorescent spherical zones. Preferably, the essentially uniform staining is combined with one or more fluorescent spherical zones having an outer diameter essentially equal to the diameter of the microsphere itself (shallowly stained).

In one embodiment of the invention, more than one fluorescent spherical zone is spatially coincident and yet each spherical zone displays detectably distinct spectral properties. In another embodiment, the spectral properties of a single distinct fluorescent spherical zone are due to the presence of a series of fluorescent dyes selected so as to undergo significant energy transfer. In this embodiment, the series of dyes comprises an initial donor dye having a desired excitation peak and final acceptor dye having a desired emission peak, where each dye in the series has a spectral overlap sufficient to allow for significant energy transfer of excitation energy. In one embodiment, the series of dyes is selected so that excitation of the microsphere at 488 nm results in a fluorescence emission at between 630 and 680 nm. Microspheres of the invention that possess fluorescent spherical zones labeled in this manner possess extended and readily controllable Stokes Shifts. Fluorescent microspheres that are uniformly stained with such an energy transfer dye series have been described in U.S. Pat. Nos. 5,326,692 to Brinkley et al. (1994) and 5,573,909 to Singer et al. (1996), both incorporated by reference.

In all embodiments of the invention, the microspheres of the invention optionally further comprise a member of a specific binding pair that is bound covalently or is noncovalently adsorbed onto the surface of the microsphere, or other surface modifications.

Suitable Microspheres

Preferably the microspheres of the present invention are highly uniform; that is for a given batch of microspheres, the individual microspheres within the batch will be essentially identical. This uniformity is typically measured using the standard deviation, or by the coefficient of variation (CV). The coefficient of variation for the microspheres of the invention is typically about 1–3%, depending upon the size of the particular microspheres.

The polymeric microspheres of the present invention may be prepared from a variety of compositions including, but not limited to, polymers and copolymers of styrenes and divinyl benzenes; an acrylate or methacrylate ester; an acrylic acid or methacrylic acid; an acrylamide or methacrylamino; an acrylonitrile or methacrylonitrile; vinyl and vinylidene halides, esters and ethers; alkenes, including ethylene, propylene, butadiene and isoprene; epoxides and urethanes. Preferably the microspheres are polystyrene or predominantly polystyrene microspheres that are optionally crosslinked such as by the incorporation of divinylbenzene during the polymerization reaction.

In one embodiment, a polymeric microsphere core is optionally coated with a polymer having a different composition, so as to modify the surface properties of the resulting microsphere, or to modify the ability of the microsphere to absorb a desired dye composition.

Unstained microspheres in a variety of sizes and polymer compositions that are suitable for preparation of fluorescent microspheres of the invention are available from a variety of sources, including: Interfacial Dynamics Corporation (Portland, Oreg.), Bangs Laboratories (Carmel, Ind.), Dynal (Great Neck, N.Y.), Polysciences (Warrington, Pa.), Seradyne (Indianapolis, Ind.), Magsphere (Pasadena, Calif.), Duke Scientific Corporation (Palo Alto, Calif.), Spherotech Inc. (Libertyville, Ill.) and Rhone-Poulenc (Paris, France). Chemical monomers for preparation of microspheres are available from numerous sources.

Preparing the Fluorescent Microsphere

Fluorescent dyes have been incorporated into uniform microspheres in a variety of ways, for example by copolymerization of the fluorescent dye into the microspheres during manufacture (U.S. Pat. No. 4,609,689 to Schwartz et al. (1975), U.S. Pat. No. 4,326,008 to Rembaum (1982), both incorporated by reference); by entrapment of the fluorescent dye into the microspheres during the polymerization process; or by non-covalent incorporation of the fluorescent dye into previously prepared microspheres (U.S. Pat. No. 5,326,692, supra; Copending application Ser. No. 08/484,151 by Haugland et al., filed Jun. 7, 1995, both incorporated by reference). Each of these methods has previously been used to produce microparticles that are internally stained essentially throughout the interior of the particle.

The two basic means of preparing the microspheres of the invention are as follows: 1) bath dying of unstained or selectively stained microspheres; 2) Copolymerization of a fluorescent or non-fluorescent monomer onto the surface of an unstained or selectively stained microsphere. The above two techniques, when used alone or in combination, produce a variety of staining patterns within the subject microspheres.

Bath Dying.

Bath dying refers to the absorption of a dye or dyes into the microsphere directly from solvent. Somewhat hydrophobic fluorescent dyes, being freely soluble in organic solvents and very sparingly soluble in water, are readily introduced by solvent-based addition of the dye to previously formed microspheres.

Bath dying has previously been used to produce fluorescent (and colored) microspheres without regard to producing a specific spherical staining pattern of staining. Novel bath-staining techniques as described in the invention are required to prevent substantial penetration of the dye into the microspheres in order to produce a distinct spherical zone near the surface of the microsphere. In particular, a variety of parameters must be carefully controlled in order for distinct shallow staining to occur, including solvent polarity, the complete absence of water in the staining solution, the physical characteristics of the dyes utilized, the composition of the microsphere, and the staining duration.

The solvent combination utilized for the staining solution must swell polymeric matrix of the microspheres enough so that staining is controlled, but not enough to permanently damage the microsphere itself, or to allow excessive amounts of fluorescent dye already present to 'bleed' from the microsphere. The degree of swelling of the microspheres is typically manipulated by controlling the amount of chlorinated organic solvent present in the staining solution. Chlorinated solvents include, among others, methylene chloride and chloroform, preferably methylene chloride. While for uniform staining of the microspheres, the staining solution contains 25% or more chlorinated solvent, preferably greater than 30%, but for applying shallow staining the staining solution must contain less than 25% chlorinated solvent, preferably less than 20%.

The shallow staining must occur under strictly anhydrous conditions. The presence of water during the shallow staining procedure typically causes precipitation of the fluorescent dye, and agglutination of the microspheres. Compensation for the presence of water by the addition of more chlorinated solvent results in excessive swelling of the microspheres resulting in a complete loss of shallow staining, and permanent damage to the microsphere. All traces of water must be carefully excluded from the staining solution in order to achieve shallow staining.

Fluorescent dyes used for shallow staining must be selected to have hydrophobicities and steric properties consistent with the staining requirements. In particular, the dyes must be largely nonpolar (electrically neutral), and possess a structural geometry consistent with intercalation into the polymeric matrix. Extremely large or excessively bulky dyes will be prevented from diffusing into the microsphere interior, while dyes that are not sufficiently hydrophobic will fail to be well-retained after dye preparation, in both cases resulting in inferior shallow staining.

Similarly, a dye selected as a uniform stain for the interior of the microsphere must be both hydrophobic and sterically bulky enough to resist diffusion out of the microsphere during the brief exposure to solvents while the shallow staining is being performed.

In principle, the microspheres must remain in contact with the staining solution long enough for the suspension to become essentially homogeneous, and for the desired degree of staining to occur. While precisely defined staining times are not needed, staining times of less than 10 minutes are typically utilized, more typically less than 5 minutes, and preferably the microspheres are kept in the staining solution for about 1 minute.

Bath dying can utilize a single dye (Example 4–7) or, multiple dyes may be used to produce spherical zones that are partially or fully coincident (Examples 1–3). Multiple dyes are also utilized to produce extensive energy transfer within the stained region, mixing the dyes in the dying solution according to ratios selected to give desired combinations of spectral properties.

Polymerization onto an existing core

It is common for unstained microspheres that have a uniform diameter to be prepared through multiple polymerization reactions, each successive step adding new coating to the surface of the microsphere (Bangs, UNIFORM LATEX PARTICLES, 1984, Seragen, Inc.). This multi-step process is typically used to produce uniform microspheres having a diameter greater than about 4 μm. Modification of this method of microsphere preparation can be used to produce microspheres with one or more fluorescent spherical zones. This method is particularly useful for producing one or more discrete fluorescent zones that are well within the microsphere, for example by selection of either fluorescent or non-fluorescent monomers for additional polymerization steps.

Preparing microspheres with nonfluorescent cores is analogous to preparing those with fluorescent cores except that the initial microsphere is essentially nonfluorescent or already contains a fluorescent spherical zone. When a nonfluorescent core is coated with a fluorescent monomer (or monomers) then a similar pattern of ring staining at or near the surface is observed as is produced using bath dying. Utilizing copolymerization of a fluorescent monomer on a nonfluorescent core has the advantage that the resulting spherical fluorescent zones do not diffuse either deeper into (or out of) the microsphere.

Combined Techniques

The two techniques may be combined to produce exceptionally powerful methods for producing a desired staining pattern in the subject microsphere. As bath dying is typically utilized to produce a shallowly stained microsphere, a microsphere may be bath dyed to produce a narrow spherical zone of fluorescent labeling, followed by copolymerization of additional fluorescent or nonfluorescent monomer to produce an internal fluorescent spherical zone. The resulting microsphere can then be subjected to bath dying again to produce additional distinct shallow staining.

In an additional embodiment, polymeric cores that are relatively impermeant to dye absorption from solvent are coated in a subsequent polymerization step with a second layer that is more receptive to bath dying. The core of such a microsphere may be selected so as to retard or prevent subsequent migration of dye further into the interior of the microsphere. In yet another embodiment of the invention, the core of the microsphere is paramagnetic and fluorescent or nonfluorescent and also contains a shallow ring stain.

In each embodiment of the invention, the microparticles utilized for the invention can be prepared or purchased with a variety of surface properties, with functional groups including, but not limited to sulfate, phosphate, hydroxyl, carboxyl, ester, amide, amidine, amine, sulfhydryl and aldehyde. If required, some of these groups may be activated for coupling to members of specific binding pairs or other surfaces. The surface groups can also be selected so as to give the particles desired physical characteristics, such as varying degrees of hydrophilicity, or to provide another means of attachment for a member of a specific binding pair.

Dye Selection

Where the fluorescent microspheres of the invention are prepared by bath dying a pre-formed and unstained microsphere, the microspheres are typically stained using electrically neutral dyes that are generally hydrophobic. Where the microspheres of the invention are prepared by copolymerization of a fluorescent monomer with a nonfluorescent monomer (or monomers) the dye is required to have a functional group that will participate in the polymerization reaction so as to become covalently incorporated in the microsphere. These functional groups include but are not limited to fluorescent derivatives of styrenes and divinyl benzenes; acrylate and methacrylate acids, esters, amides and nitriles; vinyl and vinylidene halides, esters and ethers; alkenes, including ethylene, propylene, butadiene and isoprene; epoxides and isocyanates. In the case of fluorescent monomers while it is preferable that the dye be electrically neutral, it is not strictly essential.

The dye or dyes selected for incorporation into the microparticles are typically selected based upon the desired excitation and emission spectral properties, that are readily determined by conventional means. The spectral properties of the fluorescent dyes should be determined in the polymeric materials in which they will be used. The excitation peak(s) of a dye can be approximately determined by recording an absorption spectrum on an absorption spectrophotometer or, more exactly, by running a fluorescent excitation spectrum using a scanning fluorescence spectrophotometer. The emission peak of the dye may also be determined using a fluorescence spectrophotometer to get an emission spectrum using a scanning fluorometer. The quantum yield of a candidate dye is typically determined by measuring with a fluorometer the total fluorescence emission of the dye in the desired polymer matrix, along with that of a reference dye with known absorbances at the excitation wavelength. The extinction coefficient is typically determined for a free dye in solution by using a spectrophotometer to measure absorbance of a solution with a gravimetrically determined concentration and calculating the extinction coefficient based on the Beer-Lambert law.

Once the spectral characteristics of a dye are determined in polymeric materials, as described above, those characteristics can be used to select the optimal dye or dye combination for a given application, taking into account the excitation source to be used, the available detection system, and the environment in which the materials will be used. Dyes useful for the invention generally have a quantum yield of greater than about 0.2 in the microsphere, preferably greater than about 0.5, as well as an extinction coefficient of greater than about 20,000 cm$^{-1}$M$^{-1}$, preferably greater than about 50,000 cm$^{-1}$M$^{-1}$. Dyes with lower quantum yields or lower extinction coefficients may be useful provided that sufficient concentrations can be incorporated within the microsphere so as to yield detectable fluorescent rings and/or disks.

Dyes that absorb light at the wavelengths of the principal excitation sources used in microscopy, and in particular those utilized for confocal laser scanning microscopy, are of particular importance for preparation of the fluorescent microspheres of the invention. These preferred absorbance wavelengths include those corresponding to the emission of the argon-ion laser (especially 350–360 nm, 454 nm, 488 nm and 514 nm), the krypton-ion laser (especially 568 nm and 647 nm), helium-neon lasers (especially 543 nm, 592 nm and 633 nm), mercury arc lamps (especially near 365 nm and 545 nm) and various other excitation sources, including laser diodes, frequency-doubled lasers and other light sources.

The polymeric microspheres of the present invention that are efficiently excited at wavelengths from the ultraviolet region to about 480 nm can be prepared using a wide variety of electrically neutral dyes. Many of these are known and widely used as laser dyes such as those commercially available from Lambda Electronics (Melville, N.Y.) and by Exciton. Useful dyes include, but are not limited to, naphthalenes, anthracenes, phenanthrenes, indoles, carbazoles, stilbenes, benzimidazoles, benzoxazoles, benzothiazoles, quinolines, benzoxanthrones, oxazoles, isoxazoles, oxadiazoles, benzofurans, pyrenes, perylenes, coronenes, coumarins, carbostyryls, bimanes, acridines, polyphenylenes such as terphenyl, alkenyl and polyalkenyl dyes (including 1,6-diphenyl-1,3,5-hexatriene and 1,1,4,4-tetraphenyl-1,3-butadiene) and others.

Other long wavelength dyes such as luminescent phenoxazones, oxazines and pyronines (including nile red); porphines, porphyrins, phthallocyanines and their metallated complexes, including complexes with rare earth ions such as Eu$^{3+}$ and Tb$^{3+}$; xanthenes (including fluoresceins and rhodamines); cyanine, carbocyanines and merocyanines (including styryl dyes; hydrocarbon derivatives such as rubrenes and azulenes; are suitable provided that they are either electrically neutral; or their ionic charges are balanced by lipophilic counterions that include but are not limited to lipophilic ammonium salts (such as hexadecyltrimethylammonium or benzyltrimethylammonium), fatty acids, fatty sulfonic acids or fatty sulfates (such as sodium dodecyl sulfate), detergents such as anionic or cationic derivatives of cholic acids, tetraarylphosphonium or tetraarylboride; or they contain a suitable functional group (as described above) for copolymerization.

The derivatives of the polyaza-s-indacene family of dyes known as dipyrromethaneboron difluoride dyes possess advantageous spectral data and other properties that result in superior performance when incorporated into polymeric microspheres (U.S. Pat. No. 5,326,692, supra; Copending application Ser. No. 08/484,151 supra)). These dyes are both electrically neutral and lipophilic and possess long wavelength absorption and emission bands that are easily tuned by chemical modifications to the dyes. A wide range of dipyrromethaneboron difluoride dyes are commercially available under the trademark BODIPY (Molecular Probes, Inc., Eugene Oreg.); and their synthesis is now well-documented in scientific and patent literature, including U.S. Pat. No. 4,774,339 to Haugland, et al. (1988); U.S. Pat. No. 4,916,711 to Boyer, et al. (1990); U.S. Pat. No. 5,187,288 to Kang et al. (1993); U.S. Pat. No. 5,248,782 to Haugland, et al. (1993); U.S. Pat. No. 5,274,113 to Kang, et al. (1993); U.S. Pat. No. 5,326,692 to Brinkley, et al. (1994); U.S. Pat. No. 5,338,854 to Kang, et al. (1994); U.S. Pat. No. 5,433,896 to Kang, et al. (1995); U.S. Pat. No. 5,189,029 to Boyer et al. (1993); and in U.S. Pat. No. 5,446,157 to Morgan et al. (1995), all incorporated by reference. A variety of dyes suitable for copolymerization are described, including polyaza-s-indacene dyes (Jones et al. PROC. INT. CONF. LASERS, 18, 375 (1996); PROC. SPIE 2968, 65 (1996)), coumarin dyes (U.S. Pat. No. 5,286,803 to Lindsay et al.

(1994)), and rhodamines (U.S. Pat. No. 5,136,005 to Hermes, (1992)), or are readily prepared by methods well-known in the art.

In one embodiment of the invention, novel fluorescent materials are prepared from two or more polyaza-s-indacene dyes, preferably diaza-s-indacene or triaza-s-indacene (i.e. derivatives of 4,4-difluoro-4-bora-3a,4a-diaza-s-indacene or 4,4-difluoro-4-bora-3a,4a,8-triaza-s-indacene). Polyaza-s-indacene derivatives suitable for preparation of fluorescent polymer microparticles according to this invention have the general structure of formula (I):

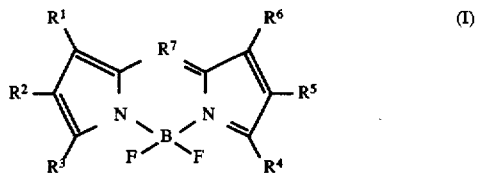

wherein $R^1$–$R^6$, which may be the same or different, are hydrogen, halogen, nitro, sulfo, cyano, alkyl, perfluoroalkyl, alkoxy, alkenyl, alkynyl, cycloalkyl, arylalkyl, acyl (wherein the alkyl portions of each contain fewer than 20 carbons, typically fewer than 10 carbons); or substituted or unsubstituted aryl or heteroaryl. Typically, no more than four of $R^1$–$R^6$, which may be the same or different, are non-hydrogen. If the polyaza-s-indacene dye is to be incorporated by staining from a bath then none of $R^1$–$R^6$ is sulfo. If the polyaza-s-indacene dye is to be incorporated into the microsphere during a copolymerization reaction then one of $R^1$–$R^6$ is required to be modified so as to incorporate a styrene; an acrylate or methacrylate acid, ester, amide or nitrile; a vinyl or vinylidene halide, ester or ether; an alkene or diene; an epoxide or an isocyanate.

$R^7$ is nitrogen; or methine; or halogen-, cyano-, alkyl-, perfluoroalkyl-, alkoxy-, alkenyl-, alkynyl-, cycloalkyl-, arylalkyl-, acyl- (wherein the alkyl portions of each contain fewer than 20 carbons, typically fewer than 10 carbons), aryl- or heteroaryl-substituted methine. Typically $R_7$ is unsubstituted methine (C—H) or nitrogen.

Alternatively, $R^7$ is methine; or alkyl-, perfluoroalkyl-, cycloalkyl-substituted methine (wherein the alkyl portions of each contain fewer than 20 carbons); or aryl- or heteroaryl- substituted methine; and adjacent substituents $R^1$–$R^2$, and $R^5$–$R^6$, taken in combination form a fused benzo ring according to the formula (II):

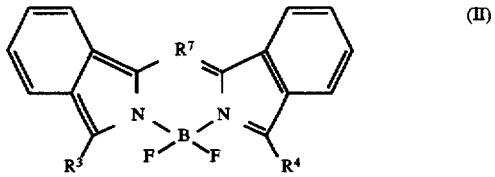

where each fused benzo ring optionally contains substituents, which may be the same or different, that are hydrogen, halogen, cyano, alkyl, perfluoroalkyl, alkoxy, alkenyl, alkynyl, cycloalkyl, alkylthio, alkylamido; or substituted or unsubstituted aryl, heteroaryl, aryl-amido, heteroaryl-amido, aryl-oxy, heteroaryl-oxy, aryl-amino, or heteroaryl-amino; or 1–2 additional fused benzo or heteroaromatic rings that are optionally unsubstituted or substituted as described above for $R^1$–$R^6$ substituents, including substituents that permit copolymerization of suitably substituted fluorescent monomers.

Where the dipyrrometheneboron difluoride dye of the invention has the structure of formula II, substituents $R^3$ and $R^4$ are independently alkyl, cycloalkyl, perfluoroalkyl, aryl or heteroaryl.

As used herein, aryl is defined as an aromatic or polyaromatic substituent containing 1 to 4 aromatic rings having 6 conjugated carbon atoms and no heteroatoms that are optionally fused to each other or bonded to each other by carbon-carbon single bonds and attached by a single bond. Heteroaryl is defined as a 5- or 6-membered aromatic heterocycle that is optionally fused to additional six-membered aromatic rings, or is fused to one 5- or 6-membered heteroaromatic ring, said heteroaromatic rings contain at least 1 and as many as 3 heteroatoms that are selected from the group consisting of O, N or S in any combination, where the heteroaryl group is attached by a single bond. Both aryl and heteroaryl groups are optionally substituted by additional bathochromic substituents that are 1–2 aryl or heteroaryl substituents bound in series, that are separated by covalent bonds or by ethenyl, butadienyl or hexatrienyl linkages. Polyaza-s-indacene dyes having the structure given in formula II that are further substituted by aryl or heteroaryl groups that are substituted by 1–2 additional bathochromic substituents possess very long-wavelength fluorescence emission properties. Such dyes typically possess emissions in the infrared region. These long-wavelength dyes, and their use to label microspheres, has been described in U.S. Provisional application Ser. No. 60/017,716, filed May 15, 1996 by Wu et al., hereby incorporated by reference.

Preferred dyes for the preparation of the microspheres of the present invention are selected from the following:

1,6-diphenyl-1,3,5-hexatriene
1,1,4,4-tetraphenyl-1,3-butadiene
nile red
coumarin 138
coumarin 314
coumarin 6
naphthalene
anthracene
phenanthrene
stilbene
benzimidazole
benzoxazole
benzothiazole
benzoxanthrone
pyrene
perylene
coronene
bimane
acridine
4,4-difluoro-1,3,5,7,8-pentamethyl-4-bora-3a,4a-diaza-s-indacene
4,4-difluoro-1,3-dimethyl-5,7-diphenyl-4-bora-3a,4a-diaza-s-indacene
4,4-difluoro-1,3,5,7-tetraphenyl-4-bora-3a,4a,8-triaza-s-indacene
4,4-difluoro-1,3-diphenyl-5-(2-pyrrolyl)-4-bora-3a,4a-diaza-s-indacene
4,4-difluoro-1,3-dipropyl-4-bora-3a,4a-diaza-s-indacene
4,4-difluoro-1,3-diphenyl-5,7-dipropyl-4-bora-3a,4a-diaza-s-indacene
4,4-difluoro-1-phenyl-3-(4-methoxyphenyl)-5-(2-pyrrolyl)-4-bora-3a,4a-diaza-s-indacene
difluoro(1-((3-(4-methoxyphenyl)-2H-isoindol-1-yl)methylene)-3-(4-methoxyphenyl)-1H-isoindolato-$N^1$,$N^2$) boron
difluoro(5-methoxy-1-((5-methoxy-3-(4-methoxyphenyl)-2H-isoindol-1-yl)methylene)-3-(4-methoxyphenyl)-1H-isoindolato-$N^1$,$N^2$)boron
4,4-difluoro-2-ethyl-1,3,5,7,8-pentamethyl-4-bora-3a,4a-diaza-s-indacene 4,4-difluoro-1,3-dimethyl-5-styryl-4-bora-3a,4a-diaza-s-indacene 4,4-difluoro-3,5-di(4-methoxyphenyl)-4-bora-3a,4a-diaza-s-indacene 3-decyl-4,4-difluoro-5-styryl-4-bora-3a,4a-diaza-s-indacene 4,4-difluoro-1,3-dimethyl-5-(4-methoxyphenyl)-4-bora-3a,4a-diaza-s-indacene 4,4-difluoro-1,3-dimethyl-5-(2-thienyl)-4-bora-3a,4a-diaza-s-indacene difluoro(1-((3-(2-(5-hexyl)thienyl)-2H-isoindol-1-yl)methylene)-3-(2-(5-hexyl)thienyl)-1H-isoindolato-$N^1$,$N^2$)boron 4,4-difluoro-1,3,5,7-tetraphenyl-4-bora-3a,4a-diaza-s-indacene 4,4-difluoro-1,3-dimethyl-5-(2-(5-methoxycarbonyl-4-methyl-2-oxazolyl)ethenyl)-4-bora-3a,4a-diazasindacene difluoro(5-methoxy-1-((5-methoxy-3-(2-(5-(4-methoxyphenyl))thienyl)-2H-isoindol-1-yl)methylene)-3-(2-(5-(4-methoxyphenyl))thienyl)-1H-isoindolato-$N^1$,$N^2$)boron

Specific Binding Pair Members

In one aspect of the invention, the surface of the microsphere of the invention is modified to be covalently or noncovalently attached to a member of a specific binding pair. Each specific binding pair member has an area on the surface or in a cavity that specifically binds to and is complementary with a particular spatial and polar organization of its complementary specific binding pair member. A specific binding pair member can be a ligand or a receptor. As used in this document, the term ligand means any organic compound for which a receptor naturally exists or can be prepared. A receptor is any compound or composition capable of recognizing a spatial or polar organization of a molecule, e.g. epitopic or determinant site. Ligands for which naturally occurring receptors exist include natural and synthetic peptides and proteins, including avidin and streptavidin, antibodies, enzymes, and hormones; nucleotides and natural or synthetic oligonucleotides, including primers for RNA and single- and double-stranded DNA; polysaccharides and carbohydrates. Representative specific binding pairs are shown in Table 1.

TABLE 1

| Representative Specific Binding Pairs | |
|---|---|
| antigen | antibody |
| biotin | avidin (or streptavidin) |
| IgG* | protein A or protein G |
| drug receptor | drug |
| toxin receptor | toxin |
| carbohydrate | lectin |
| peptide receptor | peptide |
| protein receptor | protein |
| carbohydrate receptor | carbohydrate |
| DNA (RNA) | aDNA (aRNA)† |
| enzyme | substrate |

*IgG is an immunoglobulin
†aDNA and aRNA are the antisense (complementary) strands used for hybridization In one aspect of the invention, the specific binding pair member is an antibody or antibody fragment, avidin or streptavidin. In this embodiment of the invention, the complementary binding pair member is typically a hapten, including drugs, an antigen or a biotin. Where the complementary binding pair member is a hapten, the hapten typically has a molecular weight less than 1000 daltons. In another aspect of the invention, the specific binding pair member is an oligonucleotide or nucleic acid polymer. Optionally, the complementary binding pair member is present in a cell, bacteria, virus or yeast cell such as an Fc receptor. Alternatively, the complementary member is immobilized on a solid or semi-solid surface, such as a polymer, polymeric membrane (such as polyvinylidene difluoride or nitrocellulose) or polymeric particle (such as an additional microsphere), a microchip array, or in a semi-solid matrix (such as an electrophoretic gel).

Preferably, the microspheres of the invention that are derivatized with a specific binding pair member are useful for detecting and optionally quantifying the presence of the complementary specific binding pair member in a sample, by methods that are well known in the art. Once the complementary specific binding pair member has been labeled with the microsphere of the invention, the staining pattern of the microsphere serves as an identifying marker, indicating which specific binding pair member(s) exhibited specificity for the complementary member.

Microsphere Kits

The diversity of staining patterns that can be created using fluorescent microspheres of the invention makes it possible to prepare kits for tagging samples that comprise at least two groups of labeled microspheres, the contents of each group comprising microspheres possessing a specific combination of staining pattern (including ring width, ring intensity, overlaps of rings, diameters of disks, and spectral properties of each feature) and microsphere size. Preferably all microspheres in each group come from a single production lot of the labeled microspheres and a sample of each group is retained for later comparison with the original sample to verify a match. Such sample groups or microspheres are useful as tagging reagents, as detection reagents, for combinatorial synthesis, or as tracers such as for monitoring water or air flow. Any or all of the microspheres optionally further comprise a member of a specific binding pair whose presence is correlated with the staining pattern and is determined as part of the manufacturing process.

The separately determinable groups of microspheres are in a single container, or are optionally combined in known proportions within any container or containers in the kit and it is a combination of the staining patterns of the various microspheres and their relative portions in the mixture that permits subsequent identification of which group or groups was used as a tagging reagent, detection reagent or tracer.

Where the microspheres of the invention are used to tag a sample, the staining pattern of a specific microsphere is readily determined utilizing conventional three-dimensional microscopy, preferably confocal laser scanning microscopes.

Use of Microspheres as Tagging Agents and Tracers

In one aspect of the invention the microspheres are used as tagging agents or tracers so as to be used to subsequently identify a material that has been labeled or a process that is being traced. In this application the presence of microspheres having a specified staining pattern is determined using a microscope that permits optical sectioning of the microsphere. As discussed above, the availability of a diverse array of microspheres possessing a variety of individually distinct staining patterns makes the microspheres useful, for instance, in detecting explosives or counterfeit goods, such as cosmetics, garments or currency. In another aspect of the invention, the presence, location and concentration of multiple highly distinctive microspheres are used to assess whether the specified aspects of a process were carried out, including whether the desired relative proportions of components were correctly combined during the process (e.g. assessing manufacturing, testing, or application of pesticides or herbicides on crops). Alternatively, distinctive microspheres of the invention are used to trace the flow of a fluid or gas, such as in ground-water studies, assessment of pollution sources or studies of inhalation or blood flow in animals.

When used as tagging or tracing agents, at least one distinctive microsphere of the invention, preferably a plurality of microspheres, is added to the material to be tagged or traced. In one embodiment, the microspheres are mixed to near homogeneity with the entire material. In another embodiment, the microspheres are applied to a specific portion of the material, such as a particular spot on a garment before its sale. The location of the spheres on a tagged item can be a further indication of authenticity of the item. The amount applied to the sample is typically insufficient to be visible to an unaided eye. The minimum amount required for such use is that amount sufficient for observation under a confocal laser scanning microscope (approximately 5 µL of a sample containing greater than about 100 beads). The sample is typically collected from the tagged material by washing the item with water, followed, if necessary, by centrifugation to concentrate the sample. If required, stained microspheres are separated from larger or smaller contaminants in the sample by appropriate filtration. Where the microspheres of the invention are polystyrene microspheres, they are optionally treated with a room temperature hydroxide solution to digest associated organic matter; this treatment typically does not affect the dyes incorporated within the microspheres. However, such treatment is typically useful when the microspheres are used for inhalation or blood flow studies.

Labels for Combinatorial Analysis

The microspheres of the present invention are particularly useful as tagging agents where a large library of peptide or protein sequences, oligonucleotide sequences, or potential drugs is being screened for specificity with a particular binding site. Using conventional combinatorial and sequencing methods, a large variety of potential binding pair members for a target of interest can be prepared, e.g. by synthesis on the surface of the microsphere or by coupling the binding pair member to the microsphere postsynthesis. Each distinct potential binding pair member is labeled with a microsphere possessing a specific combination of distinct internal staining patterns, intensities and other distinguishable properties. It is then possible to add a large number of potential binding pair members to the target of interest (optionally immobilized on a surface), allow sufficient time to form a complex, and then remove those potential binding pair members that failed to form a stable complex by washing. A microscopic examination of the target reveals the presence of any microsphere-labeled binding pair members complexed with the target, while a subsequent examination of the bound microspheres in optical cross-section reveals the distinctive "coding" that particularly identifies the successful binding pair sequence.

Instrument Evaluation and Correction

The microspheres of the present invention possess utility for improving the performance of any instrument capable of three-dimensional spatial analysis. While confocal laser scanning microscopy is the apparently the most common instrument used for three-dimensional analysis, any other method of microscopy that yields three-dimensional information about a specimen, such as wide-field microscopy coupled with image deconvolution, can be evaluated and/or calibrated using the microspheres of the invention.

The microspheres essentially function as microscopic three-dimensional gauges. Microspheres are isotropic, i.e. their staining pattern does not depend on the orientation of the microsphere with respect to the illumination utilized. Upon examination of the microsphere, as processed by the instrument to be evaluated, any deviation of the staining pattern from the known characteristics of the microsphere indicates inaccuracy in either the physical optics of the instrument, the data acquisition parameters, or in post-acquisition data analysis.

For evaluating and calibrating an instrument, the instrument is first used to generate a three-dimensional representation of one or more microspheres of the present invention. The three-dimensional representation can be, for example, an actual optical image, and electronic image, a set of optical cross-sections, or a three-dimensional data array. The three-dimensional representation is then compared with the expected three-dimensional representation, which is based on knowledge of the actual physical and spectral characteristics of the microspheres. In comparing the experimental data with the expected result, the performance of specific operating parameters of the instrument can be evaluated. Once the instrument has been evaluated, the operating parameters of the instrument are then adjusted so to make the three-dimensional representation more accurate with respect to the known physical and spectral characteristics of the microsphere (e.g., restoring the circularity of the image, or correcting a lack of superimposition).

In one aspect of the invention, the microspheres are used to evaluate, align, and calibrate the optical elements of the instrument, from the objective lens to the detector. By optical elements is meant both the excitation and collection optics. Elements of the optical path subject to adjustment or evaluation include, for example, excitation sources, lenses, relay mirrors, scanning mirrors, dichroics, beamsplitters, filter wheels and filter blocks. Examples of the types of evaluation and calibration possible include, evaluation of the objective lens to aid in appropriate lens selection, evaluation of the flatness of the optical field (or spherical aberration), evaluation of the chromatic registration in the optical field, i.e. chromatic aberration in the x-y or x-z axis, and aiding in identifying the need for correction in the ultraviolet region or other wavelengths.

It has traditionally been especially difficult for users of confocal laser scanning instruments to detect and correct for chromatic aberration along the z-axis. Certain microspheres of the invention are particularly useful in this regard. There microspheres have at least one fluorescent spherical zone that contains multiple dyes, where each dye has a different emission maximum and gives a distinct ring. Such a microsphere should yield coincident fluorescent rings in the x-y plane, at every position along the z-axis. The appearance of multiple nonsuperimposed rings in different fluorescence channels indicates chromatic aberration or misalignment of optical components and adjustments can therefore be made to restore coincidence of the rings.

In another aspect of the invention, the microspheres of the invention are used in conjunction with evaluating data acquisition parameters. For example, evaluation of image resolution, image intensity, magnification and detector sensitivity allows for acquisition parameters to be adjusted to maximize image accuracy.

In another aspect of the invention, the microspheres of the invention are utilized in conjunction with post-acquisition data analysis. For example, the microspheres of the invention are useful for facilitating image deconvolution using wide-field microscopy. Additionally, the microspheres possess utility for facilitating image correction and image reconstruction, with respect to making the x, y and z axes coincident in each emission channel. Alternatively, the microspheres are used to identify inaccuracies in volume reconstruction calculations, or to correct for errors in post-acquisition color representation.

Similarly, the microspheres of the present invention facilitate the determination of both the magnitude and anisotropy of chromatic aberration or spherical aberration, and can facilitate either physical corrections, corrections to the data acquisition parameters, or corrections to the post-acquisition data analysis to compensate for such chromatic aberration or spherical aberration.

In general, the microspheres of the invention are used to detect equipment malfunction or failure, to verify that collected data accurately represents the specimen of interest, and in general to "troubleshoot" every aspect of the instrument being utilized.

The examples below are given so as to illustrate the practice of this invention. They are not intended to limit or define the entire scope of this invention.

EXAMPLES

Example 1.

Preparation of microspheres having fluorescent blue and orange coincident ring stains:

The following stock solutions are prepared: 3-Decyl-4,4-difluoro-5-styryl-4-bora-3a,4a-diaza-s-indacene (5.0 mg; Molecular Probes Inc.) is dissolved in methylene chloride to give a stock solution having a concentration of 2.0 mg/mL (Stock solution A). 1,1,4,4-Tetraphenyl-1,3-butadiene (5.0 mg; Sigma Chemical) is dissolved in methylene chloride to give a stock solution having a concentration of 5.0 mg/mL (Stock solution B).

A 1.0 mL suspension (10% solids) of 15.0 μm microspheres (polystyrene/2% divinylbenzene; Bangs Laboratories) is placed in a test tube. Approximately 12 mL of ethanol is added to the test tube and the microspheres are resuspended. The suspension is centrifuged at 2,000×g and the supernatant liquid is carefully decanted from the pellet. This wash step is repeated twice more, taking care to prevent the microspheres from drying out, and to the resulting pellet is immediately added 1.0 mL of ethanol. To the resulting suspension is added a magnetic stir bar, and the suspension is stirred.

A ring staining solution is prepared by combining 35 μL of stock solution A, 480 μL of stock solution B, 450 μL of ethanol, and 35 μL of methylene chloride and mixing thoroughly. The staining solution is added to the stirring microsphere suspension, and the microsphere suspension is stirred for exactly 1 minute. The suspension is then quickly centrifuged for 5 seconds and the supernatant solution is discarded. The microspheres are then washed three times, as above, using methanol in place of ethanol, and with sonication of the suspension during the second wash step. The resulting microsphere pellet is then washed three more times using a 0.02% solution of TWEEN-20 (VWR Scientific) centrifuging for 1 minute in each step and with sonication of the suspension during the first and third wash. After washing is complete, the microspheres are suspended in approximately 5 mL of 0.02% TWEEN-20, carefully vacuum filtered using a polyester filter and washed with additional 0.02% TWEEN-20. The stained microspheres are then resuspended in 0.02% TWEEN-20 to the desired suspension concentration.

The resulting microspheres possess a well-defined region of shallow staining. When viewed in cross-section they display coincident ring staining that has both blue and orange fluorescence.

Example 2.

Preparation of microspheres having fluorescent green and dark red coincident ring stains:

The following stock solutions are prepared: 4,4-Difluoro-1,3-dipropyl-4-bora-3a,4a-diaza-s-indacene (5.0 mg; Molecular Probes Inc.) is dissolved in ethanol to give a stock solution having a concentration of 1.0 mg/ML (Stock solution C). 4,4-Difluoro-1,3,5,7-tetraphenyl-4-bora-3a,4a,8-triaza-s-indacene (5.0 mg; Molecular Probes Inc.) is dissolved in methylene chloride to give a stock solution having a concentration of 2.0 mg/mL (Stock solution D).

A 1.0 mL suspension of 10.0 μm microspheres is prepared for staining as described in Example 1.

The microspheres are stained and washed exactly as described in Example 1, except using a ring staining solution prepared by combining 300 μL of stock solution C, 150 μL of stock solution D, 100 μL of ethanol, and 200 μL of methylene chloride.

The resulting stained microspheres possess a well-defined region of shallow staining within the exterior surface of the microsphere. When viewed in cross-section they display coincident ring staining that has both green and dark red fluorescence.

Example 3.

Preparation of microspheres having fluorescent green, dark red and orange coincident ring stains:

Stock solutions A, C and D are prepared as in Examples 1 and 2.

A 1.0 mL suspension of 15.0 μm microspheres is prepared for staining as described in Example 1.

The microspheres are stained and washed exactly as described in Example 1, except using a ring staining solution prepared by combining 100 μL of stock solution A, 300 μL of stock solution C, 175 L of stock solution D, 200 μL of ethanol, and 45 L of methylene chloride.

The resulting stained microspheres possess a well-defined region of shallow staining within the exterior surface of the microsphere. When viewed in cross-section they display coincident ring staining that displays green, dark red and orange fluorescence.

Example 4.

Preparation of microspheres having uniform blue fluorescence and fluorescent orange ring stains:

Stock solution A is prepared as in Example 1. Stock solution E is prepared by dissolving 5.0 mg of 1,6-diphenyl-1,3,5-hexatriene in methylene chloride to give a stock solution having a concentration of 5.0 mg/mL.

A 1.0 mL suspension of 15.0 μm microspheres is prepared for staining as described in Example 1.

The uniform staining solution is prepared by combining 150 μL of stock solution E, 850 μL of methylene chloride and 1.0 mL of ethanol. The uniform staining solution is added to the stirring microsphere suspension, and the suspension is stirred for 6 minutes. The suspension is then quickly centrifuged for 5 seconds and the supernatant solution is discarded. The microspheres are then washed twice, with methanol using sonication of the suspension during the second wash step. The resulting microsphere pellet is then washed three more times using a 0.02% solution of TWEEN-20 with an increase in the centrifugation time to 1 minute and using sonication of the suspension during the first and third wash step.

The uniformly stained microspheres are then washed with ethanol and stained using the procedure described in Example 1, using a ring staining solution prepared by combining 100 μL of stock solution A, 400 μL ethanol and 200 μL of methylene chloride.

The resulting stained microspheres possess a well-defined region of shallow orange fluorescent staining, and uniform blue fluorescence throughout the microsphere. When viewed in cross-section they display blue fluorescent interiors and fluorescent orange ring staining.

Example 5.
Preparation of microspheres having uniform blue fluorescence and fluorescent green ring stains:

Stock solutions C and E are prepared as described in Examples 2 and 4.

A 1.0 mL suspension of 15.0 μm microspheres is prepared for staining as described in Example 1.

The microspheres are stained and washed exactly as described in Example 4, except using a uniform staining solution prepared by combining 150 μL of stock solution E, 1.0 mL ethanol and 850 μL of methylene chloride, and a ring staining solution prepared by combining 400 μL of stock solution C, 400 μL of ethanol, and 300 μL of methylene chloride.

The resulting stained microspheres possess a well-defined region of shallow green fluorescent staining, and uniform blue fluorescence throughout the microsphere. When viewed in cross-section they display blue fluorescent interiors and fluorescent green ring staining.

Example 6.
Preparation of microspheres having uniform dark red fluorescence and fluorescent green ring stains:

Stock solutions C and D are prepared as described in Example 2.

A 1.0 mL suspension of 15.0 μm microspheres is prepared for staining as described in Example 1.

The microspheres are stained and washed exactly as described in Example 4, except using a uniform staining solution prepared by combining 140 μL of stock solution D, 1.0 mL ethanol and 1.1 mL of methylene chloride, and a ring staining solution prepared by combining 400 μL of stock solution C and 300 μL of ethanol.

The resulting stained microspheres possess a well-defined region of shallow green fluorescent staining, and uniform dark red fluorescence throughout the microsphere. When viewed in cross-section they display red fluorescent interiors and fluorescent green ring staining.

Example 7.
Preparation of microspheres having uniform green fluorescence and fluorescent dark red ring stains:

Stock solutions C and D are prepared as described in Example 2.

A 1.0 mL suspension of 6.0 μm microspheres is prepared for staining as described in Example 1.

The microspheres are stained and washed exactly as described in Example 4, except using a uniform staining solution prepared by combining 300 μL of stock solution C, 700 μL ethanol and 1.0 mL of methylene chloride, and a ring staining solution prepared by combining 200 μL of stock solution D, 500 μL of ethanol and 200 μL of methylene chloride.

The resulting stained microspheres possess a well-defined region of shallow dark red fluorescent staining, and uniform green fluorescence throughout the microsphere. When viewed in cross-section they display green fluorescent interiors and fluorescent red ring staining.

Example 8.
Preparation of shallowly stained microspheres having 505/690 nm excitation and 690 nm emission:

The following stock solutions are prepared:

Stock solution E: 4,4-Difluoro-1,3-dipropyl-4-bora-3a,4a-diaza-s-indacene (5 mg) is dissolved in ethanol to give a stock solution having a concentration of 3.0 mg/mL.

Stock solution F: 4,4-Difluoro-1,3-diphenyl-5,7-dipropyl-4-bora-3a,4a-diaza-s-indacene (5 mg) is dissolved in methylene chloride to give a stock solution having a concentration of 3.0 mg/mL.

Stock solution G: 4,4-Difluoro-1,3,5,7-tetraphenyl-4-bora-3a,4a-diaza-s-indacene (5 mg) is dissolved in methylene chloride to give a stock solution having a concentration of 3.0 mg/mL.

Stock solution H: 4,4-Difluoro-1,3-diphenyl-5-(2-pyrrolyl)-4-bora-3a,4a-diaza-s-indacene (5 mg) is dissolved in methylene chloride to give a stock solution having a concentration of 3.0 mg/mL.

Stock solution I: 4,4-Difluoro-1,3,5,7-tetraphenyl-4-bora-3a,4a,8-triaza-s-indacene (5 mg) is dissolved in methylene chloride to give a stock solution having a concentration of 3.0 mg/mL.

A 1.0 mL suspension of 15.0 μm microspheres is prepared for staining as described in Example 1.

The microspheres are stained and washed exactly as described in Example 1, except using a ring staining solution prepared by combining 500 μL of stock solution E, 70 μL of stock solution F, 70 μL of stock solution G, 70 μL of stock solution H, and 140 μL of stock solution I.

The resulting stained microspheres possess a well-defined region of shallow staining, wherein the incorporated series of dyes undergo significant energy transfer. When viewed in cross-section, they display ring staining that has green excitation and dark red fluorescence (505 nm excitation peak and 680 nm emission).

Example 9.
Coupling of microspheres having uniform blue fluorescence and fluorescent shallow orange staining to NEUTRALITE avidin:

NEUTRALITE avidin (2 mg, Pierce) is placed in a test tube. To the aviding is added 10 mL of 100 mM sodium phosphate and 100 mM sodium chloride (pH 7.5). A stir bar is added and the solution is stirred.

Once the avidin is dissolved, a 10 mL suspension of 15.0 μm microspheres (prepared as in Example 4) (0.4% solids in 0.02% TWEEN-20) is slowly added to the reaction mixture. The mixture is stirred for an additional 2 hours or more.

The resulting coated microspheres are separated from unbound avidin by centrifugation at 2,000×g for 1 minute. The supernatant fluid is drawn off with a pipet and the labeled microspheres are resuspended in 10 mL of 50 mM sodium phosphate, 50 mM sodium chloride (pH 7.4) containing 1% bovine serum albumin and 0.02% TWEEN-20 and centrifuged again. The microspheres are washed an additional 3 times by centrifugation with 50 mM sodium phosphate, 50 mM sodium chloride (pH 7.4) containing 0.02% TWEEN-20 and resuspended the final time in 8 mL of this buffer.

It is to be understood that, while the foregoing invention has been described in detail by way of illustration and example, numerous modifications, substitutions, and alterations are possible without departing from the spirit and scope of the invention as described in the following claims.

What is claimed is:

1. A polymeric microsphere having a diameter of about 2 μm to about 100 μm, wherein an equatorial cross-section of said microsphere displays a first distinct fluorescent ring that is concentric with and within said microsphere; said ring having a width that is at least 0.2 μm and no greater than 35% of the radius of said microsphere.

2. A microsphere, as claimed in claim 1 wherein said first ring has a fluorescence intensity that, when measured at a fluorescence emission maximum of the first ring, is at least 20% greater than an adjusted average fluorescence intensity of the microsphere at said fluorescence emission maximum.

3. A microsphere, as claimed in claim 1, wherein said first ring has an outer diameter that is essentially equal to the diameter of the microsphere.

4. A microsphere, as claimed in claim 1, wherein the equatorial cross-section displays one or more additional distinct fluorescent rings that are concentric with and within said microsphere, each ring having a width that is at least 0.2 µm and no greater than 35% of the radius of said microsphere.

5. A microsphere, as claimed in claim 4, wherein the equatorial cross-section displays 1–3 additional distinct fluorescent rings that are substantially coincident with said first ring.

6. A microsphere, as claimed in claim 5, where the fluorescence emissions of each ring are selected so as to exhibit red, green, blue or yellow fluorescence.

7. A microsphere, as claimed in claim 1, wherein the equatorial cross-section additionally displays at least one fluorescent disk concentric with said microsphere, wherein each disk has a diameter of at least 0.4 µm.

8. A microsphere, as claimed in claim 7, wherein said disk has a diameter essentially equal to the diameter of said microsphere.

9. A microsphere, as claimed in claim 1, wherein said first distinct fluorescent ring is due to the presence of a series of fluorescent dyes comprising an initial donor dye with a desired excitation peak in a polymeric material and final acceptor dye with a desired emission peak in a polymeric material, and where each dye in the series has a spectral overlap sufficient to allow for significant energy transfer of excitation energy.

10. A microsphere, as claimed in claim 1, wherein said first distinct fluorescent ring is due to the presence of a polyaza-s-indacene dye.

11. A microsphere, as claimed in claim 1, wherein said first distinct fluorescent ring is due to the presence of a copolymer of a fluorescent monomer.

12. A microsphere, as claimed in claim 1, wherein said microsphere comprises a polymer or copolymer of a styrene, a divinyl benzene, an acrylate or methacrylate ester, an acrylic acid or methacrylic acid, an acrylamide or methacrylamino, an acrylonitrile or methacrylonitrile, a vinyl halide, a vinylidene halide, a vinylidene ester, a vinylidene ether, an alkene, an epoxide or a urethane.

13. A microsphere, as claimed in claim 12, wherein said microsphere comprises a polymer or copolymer of polystyrene that is optionally crosslinked through the incorporation of divinylbenzene during polymerization.

14. A microsphere, as claimed in claim 1, further comprising a member of a specific binding pair that is covalently attached or non-covalently adsorbed onto the microsphere.

15. A microsphere, as claimed in claim 1, wherein said microsphere comprises a polymer or copolymer of polystyrene that is optionally crosslinked through the incorporation of divinylbenzene during polymerization, said microsphere having a diameter of about 4 µm to about 16 µm, said first distinct fluorescent ring having an outer diameter that is essentially equal to the diameter of the microsphere, wherein the equatorial cross-section optionally displays 1–3 additional distinct fluorescent rings that are substantially coincident with said first ring.

16. A microsphere, as claimed in claim 15, wherein the equatorial cross-section additionally displays at least one fluorescent disk concentric with said microsphere, wherein each disk has a diameter of at least 0.4 µm.

17. A microsphere, as claimed in claim 15, wherein said first distinct fluorescent ring is due to the presence of a fluorescent dye that is a polyaza-s-indacene having the formula:

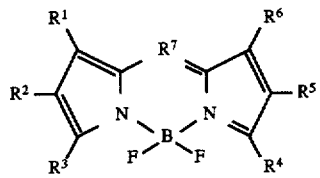

wherein $R^1$, $R^2$, $R^3$, $R^4$, $R^5$ and $R^6$, which may be the same or different, are hydrogen, halogen, alkyl, perfluoroalkyl, alkoxy, alkenyl, alkynyl, cycloalkyl, arylalkyl, or acyl, wherein the alkyl portions of each contain fewer than 20 carbons; or substituted or unsubstituted aryl or heteroaryl;

or adjacent substituents $R^1$ and $R^2$, and adjacent substituents $R^5$ and $R^6$, when taken in combination form a fused benzo ring that is optionally and independently substituted one or more times by hydrogen, halogen, alkyl, perfluoroalkyl, alkoxy, alkenyl, alkynyl, cycloalkyl, alkylthio, alkylamido, amino, monoalkylamino or dialkylamino wherein the alkyl portions of each contain fewer than 20 carbons; or by substituted or unsubstituted aryl, heteroaryl, aryl-amido, heteroarylamido, aryl-oxy, heteroaryl-oxy, aryl-amino, or heteroaryl-amino; or by 1–2 additional fused benzo or heteroaromatic rings that are optionally unsubstituted or substituted;

$R^7$ is nitrogen; or methine; or halogen-, cyano-, alkyl-, perfluoroalkyl-, alkoxy-, alkenyl-, alkynyl-, cycloalkyl-, arylalkyl-, acyl-substituted methine wherein the alkyl portions of each contain fewer than 20 carbons; or aryl- or heteroaryl-substituted methine.

18. A microsphere, as claimed in claim 15, wherein said first distinct fluorescent ring is due to the presence of a fluorescent dye that is
1,6-diphenyl-1,3,5-hexatriene,
1,1,4,4-tetraphenyl-1,3-butadiene,
nile red,
coumarin 138,
coumarin 314,
coumarin 6,
naphthalene,
anthracene,
phenanthrene,
stilbene,
benzimidazole,
benzoxazole,
benzothiazole,
benzoxanthrone,
pyrene,
perylene,
coronene,
bimane,
acridine,
4,4-difluoro-1,3,5,7,8-pentamethyl-4-bora-3a,4a-diaza-s-indacene,
4,4-difluoro-1,3-dimethyl-5,7-diphenyl-4-bora-3a,4a-diaza-s-indacene,
4,4-difluoro-1,3,5,7-tetraphenyl-4-bora-3a,4a,8-triaza-s-indacene,
4,4-difluoro-1,3-diphenyl-5-(2-pyrrolyl)-4-bora-3a,4a-diaza-s-indacene,
4,4-difluoro-1,3-dipropyl-4-bora-3a,4a-diaza-s-indacene, 4,4-difluoro-1,3-diphenyl-5,7-dipropyl-4-bora-3a,4a-diaza-s-indacene, 4,4-difluoro-1-phenyl-3-(4-methoxyphenyl)-5-(2-pyrrolyl)-4-bora-3a,4a-diaza-s-indacene, difluoro(1-((3-(4-methoxyphenyl)-2H-isoindol-1-yl)methylene)-3-(4-methoxyphenyl)-1H-isoindolato-$N^1,N^2$)boron, difluoro(5-methoxy-1-((5-methoxy-3-(4-methoxyphenyl)-2H-isoindol-1-yl)methylene)-3-(4-methoxyphenyl)-1H-isoindolato-$N^1,N^2$)boron, 4,4-difluoro-2-ethyl-1,3,5,7,8-pentamethyl-4-bora-3a,4a-diaza-s-indacene, 4,4-difluoro-1,3-dimethyl-5-styryl-4-bora-3a,4a-diaza-s-indacene, 4,4-difluoro-3,5-di(4-methoxyphenyl)-4-bora-3a,4a-diaza-s-indacene, 3-decyl-4,4-difluoro-5-styryl-4-bora-3a,4a-diaza-s-indacene, 4,4-difluoro-1,3-dimethyl-5-(4-methoxyphenyl)-4-bora-3a,4a-diaza-s-indacene, 4,4-difluoro-1,3-dimethyl-5-(2-thienyl)-4-bora-3a,4a-diaza-s-indacene, difluoro(1-((3-(2-(5-hexyl)thienyl)-2H-isoindol-1-yl)methylene)-3-(2-(5-hexyl)thienyl)-1H-isoindolato-$N^1,N^2$)boron, 4,4-difluoro-1,3,5,7-tetraphenyl-4-bora-3a,4a-diaza-s-indacene, 4,4-difluoro-1,3-dimethyl-5-(2-(5-methoxycarbonyl-4-methyl-2-oxazolyl)ethenyl)-4-bora-3a,4a-diaza-s-indacene, or difluoro(5-methoxy-1-((5-methoxy-3-(2-(5-(4-methoxyphenyl))thienyl)-2H-isoindol-1-yl)methylene)-3-(2-(5-(4-methoxyphenyl))thienyl)-1H-isoindolato-$N^1,N^2$)boron.

19. A kit, comprising:

a) a plurality of containers;

b) a group of highly uniform polymeric microspheres of a size of about 2 µm to about 100 µm within each container made up of highly uniform polymeric microspheres of substantially the same uniform size and staining pattern, with the specific combination of size and staining pattern in one group not being repeated in any other group;

wherein the polymeric microspheres within at least one container have an equatorial cross-section that displays a first distinct fluorescent ring that is concentric with and within said microsphere; said ring having a width that is at least 0.2 µm and no greater than 35% of the radius of said microsphere.

20. A kit, as claimed in claim 19, wherein each group of polymeric microspheres is covalently attached or non-covalently attached to a member of a specific binding pair, wherein the specific combination of size and staining pattern in one group corresponding to a particular member of a specific binding pair.

21. A method of improving the performance of an instrument capable of three-dimensional spatial analysis, said method comprising:

a) generating a three-dimensional representation of one or more polymeric microspheres, each microsphere having a diameter of about 2 µm to about 100 µm, wherein an equatorial cross-section of said microsphere displays a first distinct fluorescent ring that is concentric with and within said microsphere; said ring having a width that is at least 0.2 µm and no greater than 35% of the radius of said microsphere;

b) comparing said three-dimensional representation with the actual physical and spectral characteristics of said microspheres;

c) evaluating the performance of said instrument; and d) adjusting one or more operating parameters of said instrument so as to make said three-dimensional representation more accurate.

22. A method, as claimed in claim 21, wherein the adjusting step comprises adjusting one or more parameters of the optical pathway.

23. A method, as claimed in claim 22, wherein the adjusting step comprises bringing one or more components of the optical pathway into proper alignment.

24. A method, as claimed in claim 21, wherein the adjusting step comprises adjusting one or more parameters of data acquisition.

25. A method, as claimed in claim 21, wherein the adjusting step comprises adjusting one or more parameters of data analysis.

26. A method, as claimed in claim 21, wherein the adjusting step comprises adjusting one or more parameters supplied to a data deconvolution algorithm.

27. A method, as claimed in claim 21, wherein the evaluating step comprises identifying the magnitude and anisotropy of a spherical or chromatic aberration in said instrument.

28. A method, as claimed in claim 27, wherein the adjusting step comprises adjusting one or more parameters of the optical pathway, data acquisition or data analysis to correct said spherical or chromatic aberration.

* * * * *